US008337785B2

(12) United States Patent
Davies et al.

(10) Patent No.: US 8,337,785 B2

(45) Date of Patent: Dec. 25, 2012

(54) SUBSTANCE AND A DEVICE

(75) Inventors: Anthony Davies, Dublin (IE); Slobhan Mitchell, Dublin (IE); Dermot Kelleher, County Dublin (IE); Yuri Volkov, Dublin (IE)

(73) Assignee: The Provost, Fellows and Scholars of the College of the Holy and Undivided Trinity of Queen Elizabeth, Near Dublin, Dublin (IE)

( * ) Notice: Subject to any disclaimer, the term of this patent is extended or adjusted under 35 U.S.C. 154(b) by 279 days.

(21) Appl. No.: 12/450,117

(22) PCT Filed: Mar. 13, 2008

(86) PCT No.: PCT/IE2008/000020

§ 371 (c)(1), (2), (4) Date: Apr. 6, 2010

(87) PCT Pub. No.: WO2008/111035

PCT Pub. Date: Sep. 18, 2008

(65) Prior Publication Data

US 2010/0197525 A1 Aug. 5, 2010

(30) Foreign Application Priority Data

Mar. 13, 2007 (IE) .................................... 2007/0168
Mar. 13, 2007 (IE) .................................... 2007/0169

(51) Int. Cl.

*B01L 3/00* (2006.01)
*G01N 31/00* (2006.01)
*C40B 60/00* (2006.01)
*C12M 1/18* (2006.01)

(52) U.S. Cl. ........ 422/553; 422/407; 422/547; 422/548; 422/549; 422/550; 422/551; 422/552; 422/559; 506/33; 435/305.1; 435/305.2; 435/305.3; 435/305.4; 220/373; 220/374

(58) Field of Classification Search ........................ None
See application file for complete search history.

(56) References Cited

U.S. PATENT DOCUMENTS 5,587,321 A 12/1996 Smith et al.
(Continued)

FOREIGN PATENT DOCUMENTS

EP 0866119 A2 9/1998
(Continued)

OTHER PUBLICATIONS

International Search Report dated Mar. 13, 2007.

(Continued)

*Primary Examiner* — Neil N Turk
(74) *Attorney, Agent, or Firm* — Jacobson Holman PLLC

(57) ABSTRACT

A device (1) for housing a scientific sample comprising at least one sample well (2) and an on-board buffering substance (3) wherein the onboard buffering substance (3) at least partly surrounds the sample well (2). The on-board buffering substance (3) may be in the form of a matrix, such as a gel-like matrix. The device (1) may further comprise an insulating means. Also described is a substance for use in culturing and/or assaying a sample whereby the substance provides atmospheric and thermal buffering. The invention further provides a lid for a single-well or multi-well sample plate, the lid being configured to facilitate delivery of a sample through the lid into a well, and for sealing the well. The lid comprises moveable portions (52, 53) that have at least one orifice (54, 57) formed through the moveable portions (52, 53) such that a conduit is formed by alignment of the orifices (54, 57) of both the lid portions (52, 53).

26 Claims, 16 Drawing Sheets

1
26
2
26
26
3
26

U.S. PATENT DOCUMENTS

| | | | | |
|---|---|---|---|---|
| 5,955,352 | A | 9/1999 | Inoue et al. | |
| 2001/0001644 | A1 * | 5/2001 | Coffman et al. | 422/102 |
| 2004/0043494 | A1 | 3/2004 | Amorese et al. | |
| 2006/0233670 | A1 | 10/2006 | Lehto | |

FOREIGN PATENT DOCUMENTS

| | | | |
|---|---|---|---|
| JP | 10-337178 | | 12/1998 |
| JP | 2000-236869 | | 9/2000 |
| JP | 2004-537397 | A | 12/2004 |
| WO | WO 01/90721 | | 11/2001 |
| WO | WO02/100545 | A1 | 12/2002 |
| WO | WO 2005/098423 | | 10/2005 |
| WO | WO 2006/005811 | | 1/2006 |

OTHER PUBLICATIONS

Lundholt, Betina Kerstin, et al.; A Simple Technnique for Reducing Edge Effect in Cell-Based Assays; The Society for Biomolecular Screening 8(5); 2003; pp. 566-570.

* cited by examiner

SUBSTANCE AND A DEVICE

This is a national stage of PCT/IE08/000,020 filed Mar. 13, 2008 and published in English, which has a priority of Irish no. 2007/0168 filed Mar. 13, 2007 and Irish no. 2007/0169 filed Mar. 13, 2007, hereby incorporated by reference.

The present invention relates to a substance and a device for use in culturing and/or assaying samples such as biological, chemical, physical, biochemical and/or nanotechnical samples and the like.

INTRODUCTION

All chemical, biological, physiological and physical processes are influenced by environmental elements such as temperature, pH and chemical composition. Uncontrolled changes in any of these factors can exert unwanted physical, chemical and/or biological effects on the specimen/sample in question leading to poor reproducibility or disruption of a given scientific and/or manufacturing process.

With the emergence of high throughput and multiplexed biological, chemical and materials screening, the use of multi-welled assay plates has become standard for almost all automated experimental and storage applications. Conventionally cells and tissue samples are cultured in plates which typically have 96 wells or well formats of 1536-, 384-, 48- or 24-wells. However, many of these experimental procedures comprise of multiple steps requiring translocation between several different storage, processing anti experimental platforms such as plate shakers, plate readers and the like. Movement of the plate between a variety of locations subject the plate and, more importantly, samples retained in the plate to variations in environment and/or temperature fluctuations. These variations can have a detrimental effect on the samples. Fluctuations in temperature across a multi-well plate is a recognised problem and it has been well documented that standard multi-well plates suffer from an "edge effect" once the plate has been removed from an incubator.

The "edge effect" refers to the periphery of the culture device or multi-well plate which is more exposed than the centre of the culture device and therefore lose heat faster when the device is removed from an incubator. FIGS. 1 and 2 (prior art) are perspective (FIG. 1) and top plan (FIG. 2) views of a multiwell plate according to the prior art with the lid removed. It is known that the temperature of individual wells fluctuates across a multi-well plate depending on the position of the well. The well labelled A is on the extremity of the plate and the temperature of this well is lower than the temperature of wells B and C. Well C is located in the centre of the plate is one of the warmest wells. Such temperature fluctuations may be problematic when reproducible, sensitive or accurate experimental conditions are required as the temperature differential between individual wells of the same sample plate may have a significant impact on the results obtained from the experiment.

Lundhalt et al., *J. Biomol. Screening,* 2003 8(5):566-570 have devised a method of reducing the edge effect by incubating newly seeded multi-well plates at room temperature for a period of time prior to placing the plates in a $CO_2$ incubator.

A further attempt to try and minimise the impact of adverse external effects has included the use of plates which are retained inside a housing type chamber, however this equipment is bulky, cumbersome to use and costly.

There is a clear need for an improved system whereby cells and tissue samples may be grown and cultured with minimal impact from external factors.

The invention also provides a cover or lid for single well or multi well plates.

A problem which may be encountered in the growth and culturing of cells and/or tissue samples in a culture device is the need for a cover/lid and the ease of its removal, particularly when the cells and/or tissue sample are cultured in a multi-well plate. Many of the commercially available multi-well plates, for example those available from Costar®, Nunc®, Becton Dickenson® and the like, have a single lid such that the entire lid must be removed to access the wells of the plate. This type of lid is cumbersome to manipulate, especially in an aseptic tissue culture environment. In addition, removal of the entire lid exposes all of the wells of a plate to the external environment. In particular, the entire surface area of samples present in the wells is exposed to the external environment. Such exposure leaves the wells, and samples, vulnerable to contaminants for example, air-borne viruses, bacteria, fungi, dust particles and the like.

High throughput screening (HTS) techniques are used for assaying numerous samples at the same time. Such assays are generally based on samples retained in multi well plates, such as plates having 24-, 48-, 96-, 384- and 1536-well formats or the like. It is standard in such assays that the multi-well plate has a lid or cover to prevent cross contamination of samples, for example if the multi-well plate is shaken in one of the method steps, and to maintain the sterility of samples. It is particularly important to maintain sterility of samples by minimising the length of time that the sample is exposed to the external environment to reduce the likelihood of contamination of the sample with air-borne contaminants.

Given the vast number of samples screened, HTS assays are generally automated. As most of the assays performed have several different steps to the method, in an automated assay, a robot arm may transfer the multi-well plate between different stations, for example incubator stations, dispensing stations, shaking stations and the like, a number of times. Depending on the type of assay being performed, a number of different solutions will be aspirated from and dispensed into the wells of the multi-well plate. During such a step, the robotic arm must first remove the lid from the multi-well plate; thereby exposing the entire plate to the external environment, prior to aspirating and/or dispensing a solution. Removal of the lid of the multi-well plate exposes the whole surface area of each well to the external environment, thus therein lies a possibility of either the exposed samples and/or the assay machine itself being contaminated.

Thus, there is a clear need for an improved lid for a single well or multi-well sample plate that is easier to manipulate, in both an aseptic and a non-aseptic environment.

STATEMENTS OF INVENTION

In one aspect, the invention provides a device for housing a sample comprising at least one sample well and an on-board buffering substance wherein the onboard buffering substance at least partly surrounds the sample well. The device may be suitable for culturing and/or assaying a biological, chemical, physical, biochemical, nanotechnical sample or material. One of the advantages of the device is that it may be bought "off the shelf", thereby eliminating the need for the end user to prepare the device prior to use. A further advantage is that the substance can be considered as an environmental control which is incorporated into the device itself.

The substance of the device may retain its structure within the range of the operating temperature of the activity requiring the use of a multiwell plate. For example the substance may be in the form of a matrix. The substance of the device may be a solid or semi-solid at room temperature.

The substance may comprise a gel-like material. The gel-like material may be a natural gel-like material or a synthetic gel-like material. Alternatively the gel-like material may be a semi-synthetic gel like material.

The gel-like material may be a polymer.

The gel-like material may comprise one or more from the group consisting of: agar, agarose, acrylamide, and gelatine.

The gel-like material may be aqueous based.

The substance of the device may further comprise one or more additives selected from the group consisting of oxygen scavengers, exothermic compounds, endothermic compounds, dessicants, pH indicators, dyes and anti-microbial agents. One of the advantages of providing additives in the substance is that a specific micro-environment may be achieved and buffered.

The device may comprise a lid. One of the advantages of providing a lid is that the lid may cover and or shield/protect the sample retaining means from the external environment. The lid may be moveable to allow access to the sample retaining means.

The device may further comprise an insulating means. For example the insulating means may be a layer of insulating material such as polystyrene. Alternatively, the insulating means may comprise a lid.

The device may be a multi-well plate.

In a further aspect, the present invention embodies a substance for use in culturing and/or assaying a biological, chemical, physical, biochemical, nanotechnical sample or material whereby the substance provides atmospheric and thermal buffering. One of the advantages of such a substance is that the substance may reduce environmental fluctuations such as thermal fluctuations. In addition the substance may improve reproducibility of experiments and/or assays by maintaining optimal environmental conditions for the biological chemical, physical, biochemical or nanotechnical sample.

In accordance with the invention, the term physical sample may be understood to mean any sample that is not biological, chemical or biochemical, for example, crystals that may be grown and/or stored for crystallography purposes. In accordance with the present invention, the term nanotechnical sample may be understood to mean any sample having dimensions of 1-1000 nm, for example, the storage of quantum nanodots or nanoparticles prior to experimentation.

The substance may be in the form of a matrix.

The substance may be solid within the desired temperature range for the process being undertaken. For example the substance may be solid or semi-solid at room temperature. Due to the nature of substance, the end user may (in accordance with the present invention) adjust the ratios of ingredients in the receipe for the substance to obtain a substance with the desired substantially solid properly at the desired temperature range.

The substance may comprise a gel-like material. For example the gel-like material may be a natural gel-like material or a synthetic gel like material. Alternatively, the gel-like material may be semi-synthetic.

The gel-like material may be a polymer such that the material can polymerise.

The gel-like material may comprise one or more selected from the group consisting of agar, agarose, acrylamide, gelatine or the like.

The substance of the invention may further comprise one or more additives selected from the group consisting of oxygen scavengers, exothermic compounds, endothermic compounds, dessicants, pH indicators, dyes and anti-microbial agents. One of the advantages of providing additives in the substance is that a specific micro-environment may be achieved and buffered.

The substance may be placed onboard a multi-well plate.

The present invention also relates to a lid for a single-well or multi-well sample plate, the lid being configured to facilitate delivery of a sample through the lid into a well, and for sealing the well. One of the advantages of a lid according to the present invention is that the lid may not have to be removed from a sample plate when a liquid or a sample is dispensed into or aspirated from a well of a sample plate.

The lid may comprise portions which are moveable relative to one another between a sample delivery configuration and a sealed configuration. The moveable portions may have at least one orifice. A conduit may be formed by alignment of the orifices of both the lid portions. An advantage of such an arrangement is that the orifice may pass through the lid, the conduit may therefore function as a channel for example a delivery channel or access channel.

The conduit may be closed by misaligning the orifices of one lid portion with respect to the orifice of the other lid portion. One of the advantages of such a closing device is that it may be simple to use for example the lid may be closed using only one hand when the lid is used in a manual experiment. Alternatively, if the lid is used in an automated experiment, the simple closing of the lid may reduce the number of steps performed by the automated device when opening or closing the lid.

The lid may further comprise a biasing means for example the biasing means may bias the lid in a closed configuration. In one embodiment the biasing means may be a spring. One of the advantages associated with a biasing means is that the biasing means may assist in preventing or minimising unwanted opening of the lid for example during transportation or storage of the lid.

The portions of the lid may be connected to one another by a connecting means. For example the connecting means may be selected from the group comprising: rails, slides, projections from the upper lid, projections from the lower lid, and combinations thereof. Preferably the connecting means may be a tongue and groove arrangement. The connecting means may act as a mechanism by which the lid portions may move relative to one another, for example by sliding relative to one another.

The lid may further comprise a stop for restricting the amount of movement of the portions with respect to one another. One of the advantages of a stop is that it may prevent one of the lid portions from moving too much with respect to the other lid portion. For example, the stop may act as a means by which the two portions are prevented from separating.

The lid may further comprise a locking mechanism for example the mechanism may prevent the opening of the lid. Desirably, the locking mechanism may be over-ridden by the end user in a manual experiment or an automated device in an automated experiment.

The lid may be constructed of a plastics material.

Advantageously one of the portions may be formed as a single piece. Desirably one or both of the portions (outer and/or inner portion) may be formed as a single piece.

The lid may further comprise a spacing element. Advantageously, a spacing element may reduce friction between the two portions when the portions are moved relative to one another.

In a further embodiment the present invention may provide a device comprising a single-well or multi-well sample plate and a lid as described above. Advantageously, the device may be sterilised such that the device is suitable for tissue culture work in aseptic conditions or the like.

In an alternative embodiment, the present invention may provide a device for housing a scientific sample comprising at least one sample well and an on-board buffering substance wherein the onboard buffering substance comprises a gel-like material and the onboard buffering substance at least partly surrounds the sample well as described above and a lid as described above.

BRIEF DESCRIPTION OF THE DRAWINGS

The invention will be more clearly understood from the following description thereof given by way of example only, in which:—

DETAILED DESCRIPTION

Figure 1:
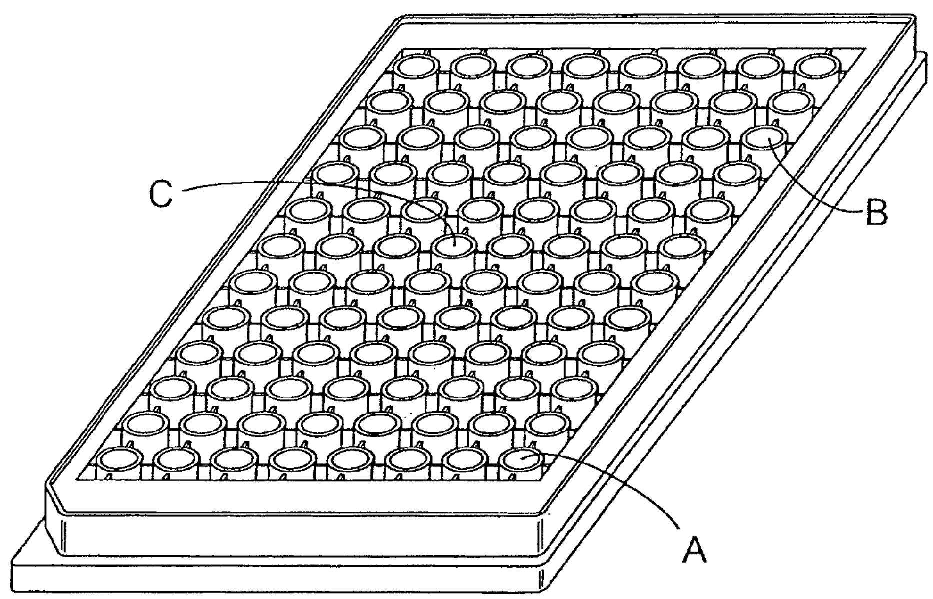
FIG. 1 (Prior art) is a perspective view of a multi-well plate according to the prior art with a lid removed.
Figure 2:
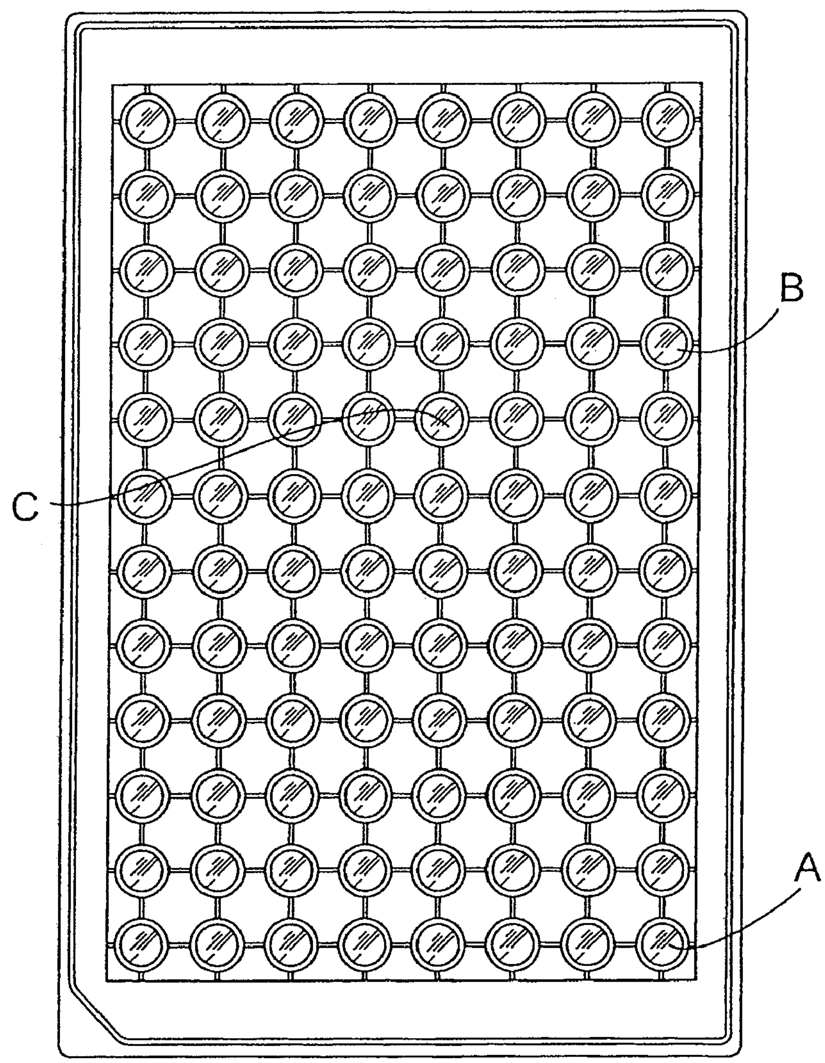
FIG. 2 (Prior art) is a top plan view of the prior art multi-well plate of FIG. 1.

The substance of the invention may be used in any activity requiring the use of a multiwell plate, for example, tissue culture, storage, transportation, liquid handling, crystallography, biomaterial warehousing, freezing samples, combinatorial chemistry, high throughput screening etc. In particular, the substance of the invention may be used in culturing and/or assaying of biological material and the like. The substance may provide atmospheric and thermal buffering of a biological material. Preferable attributes of the substance may include, but are not limited to, the following: capable of maintaining and/or modifying and/or absorbing and/or dissipating and/or generating and/or releasing thermal energy, atmospheric gasses (such as $CO_2$ $O_2$, $N_2$ and the like) and solvent vapours such as water, DMSO and organic compounds and the like. In one embodiment the substance is a polymerisable matrix. For example, the substance of the invention may be considered to be a porous matrix.

The substance may comprise a liquid, such as a viscous liquid. Alternatively, the substance may be a solid. The substance may be substantially solid at the temperature range of the activity to be carried out. For example the substance may be solid or semi-solid at room temperature. The substance may have gel like properties such that the substance can absorb shocks. For example, the substance may act as a mechanical buffer to external vibrations. The substance may absorb and/or dissipate mechanical shock, such as a mechanical shock created by an accidental knocking of a device containing the substance.

The substance may be made as a liquid solution that solidifies (polymerises) over time. Typically the substance may consist of a polymer selected from the group comprising: agarose and/or acrylamide and/or gelatine and/or agar and the like. The polymer(s) may be dissolved in a solution or solvent. For example, the polymer(s) maybe dissolved in an aqueous solution such as water.

Typically, the weight/volume (w/v) percentage concentration of an agarose matrix solution is from about 0.1% to about 10%, or from about 0.1% to about 5%, or from about 0.1% to about 2.5%. The polymer solution may be at a concentration of about 1% which will allow the agarose to have a solid or semi-solid form at the temperature of the activity, for example room temperature. As a person skilled in the art will appreciate, the concentration of polymer used depends on the consistency of the matrix required. Furthermore, the skilled person will appreciate that the environmental temperature of the room in which the matrix solution is made will affect the consistency of the polymerised matrix. For example, at higher temperatures, a higher percentage matrix solution will be required to ensure complete polymerisation of the matrix solution. Desirably, the substance may retain a polymerised (set or solid or semi-solid) state at the temperature at which the substance is to be employed in the final use.

As a person skilled in the art will appreciate the percentage concentration of polymer the substance will vary depending on the polymer(s) used and the temperature at which the substance is made. In addition, the end use temperature of the substance may have an impact on the concentration percentage of polymer in the substance. Preferably a substance with the lowest possible percentage concentration of polymer will be used. The lower the concentration of the polymer in the substance; the higher the concentration of solution/solvent in the substance. Likewise, the higher the concentration of polymer in the substance; the lower the concentration of solution/solvent in the substance (inverse relationship of polymer concentration to solution/solvent concentration). Lower percentage substances, for example 0.1-2% substance may contain more moisture than higher percentage substances, for example 8-10% substances. It is desirable that the substance contains moisture as moisture may evaporate from the substance in non-humid conditions, for example in a laboratory. Desirably, moisture may evaporate from the substance rather than the sample. For example moisture may evaporate from the substance forming a barrier vapour between the sample and external environment. The substance of the invention may also allow for the maintenance and/or modification of atmospheric gasses such as $CO_2$ $O_2$, $N_2$ etc. Desirably, the substance may also allow the donation and/or maintenance and/or saturation and/or removal of moisture from the plate environment. The moisture may be in the form of any solvent such as water or DMSO or the like.

A large range of compounds may be added to the substance (prior to polymerisation) depending on the end use of the substance. Additives may be added to the substance to allow for maximal retention of $CO_2$ such that $CO_2$ is released slowly. Anti oxidants and oxygen free radical and scavengers may also be added.

Examples of additives include:

Oxygen scavengers

Examples of oxygen scavengers include but are not limited to the following: Sulphite, catalase, carnosine, N-acetyl-camosine, Homocarnosine, carbohydrazide, oxygen scavenging enzymes, and pyrogalol.

Compounds that produce an exothermic reaction such as compounds that giveout heat.

Examples of compounds that produce an exothermic reaction include but are not limited to the following: sodium hydroxide and hydrochloric acid; glycine (glycerol) and lower polyglycols. Desirably, the reactions may be suppressed and/or activated by the end user for example by alteration of environmental conditions.

Compounds that produce an endothermic reaction such as compounds that absorb heat.

Examples of compounds that produce an endothermic reaction include but are not limited to the following: sodium hydroxide and water; citric acid and sodium hydroxide. Desirably, the reactions may be suppressed and/or activated by the end user, for example by altering environmental conditions surrounding the matrix $CO_2$ maintainers/stabilisers for example, bicarbonate of soda/scavengers, for example, soda lime.

Desiccants

Examples of desiccants include but are not limited to the following: silica gel, cobalt, chloride.

pH Indicators for example phenol red.

Dyes

Examples of dyes include but are not limited to the following: fungal dye indicators such as Remazol Brilliant Blue R(RBBR), poly R-478, guaiacol and tannic acid. Dyes may be added to the substance for use in immunofluorescence or fluorescence applications. For example, a dye may be used to minimise the exposure of a fluorescent sample to light, thereby reducing the fading effect of the fluorescence and prolonging the storage period of a fluorescent sample.

Infection indicator

For example, an early warning system for bacterial contamination.

Antimicrobial agents

Examples of antimicrobial agents include but are not limited to the following: bacteriordals, antibiotics, fungicidals, chemical inhibitors of microbial growth and the like.

The substance may also contain a combination of additives for example the matrix may contain a carbon source (such as glucose, lactose, sucrose or the like) and a pH sensitive colour indicator (such as phenol red) to indicate microbial metabolic activity in the substance. Alternatively, the substance may contain citric acid and bromothymol blue such that a colour change reaction from blue to green would occur if the substance became more alkaline due to microbial activity.

The substance of the invention has been found to influence thermal conditions in that it can retain and/or generate and/or dissipate and/or absorb heat as required.

The substance may be used in the storage of cells, tissue samples and/or synthetic chemical entities, both in the long term and short term. Use of the substance in the storage of cells may reduce the amount of degradation of the cells. Alternatively, the substance may also be used in one of the following ways: crystallography experiments; biomaterial warehousing for example use with samples stored in libraries, combinatorial chemistry such as where reactions require strict environmental conditions. In addition, the substance may be used in High throughput screening techniques. The substance may also be employed in the process of freezing down and/or thawing of cell and/or tissue samples. Use of the substance in the freezing down and/or thawing of samples may allow the sample to cool down slowly and warm up slowly thereby reducing the amount of degradation caused by freezing and thawing samples.

In a further aspect the present invention also provides a device. A device in accordance with the present invention comprises a sample retaining means and the substance. For example once the substance has been made, the substance may be dispensed, in its liquid form, into the space surrounding a sample retaining means and allowed to polymerise. Sample retaining means may be a single or multi-well plate, or a container suitable for storage of biomaterials, cells, organic or inorganic materials. Sample retaining means containing the polymerised substance may be stored for example by sealing the sample retaining means in polyethylene film. A device in accordance with the present invention may be stored at +4° C. until required. If the substance in the device includes antimicrobial agents, the device may have a longer shelf-life compared to a device in which the substance does not contain antimicrobial agents.

The device of the present invention may reduce fluctuations in external factors impacting on the growth and culturing of cells and/or tissue samples. When the substance described above is incorporated into a sample retaining device, an environmental control is incorporated into the device itself. The substance may maintain the temperature of the device for example, when the culture device is removed from an incubator or when the culture device is transported from one work station to another all the wells is maintained constant and the impact of other detrimental environmental factors are minimised.

Figure 3:
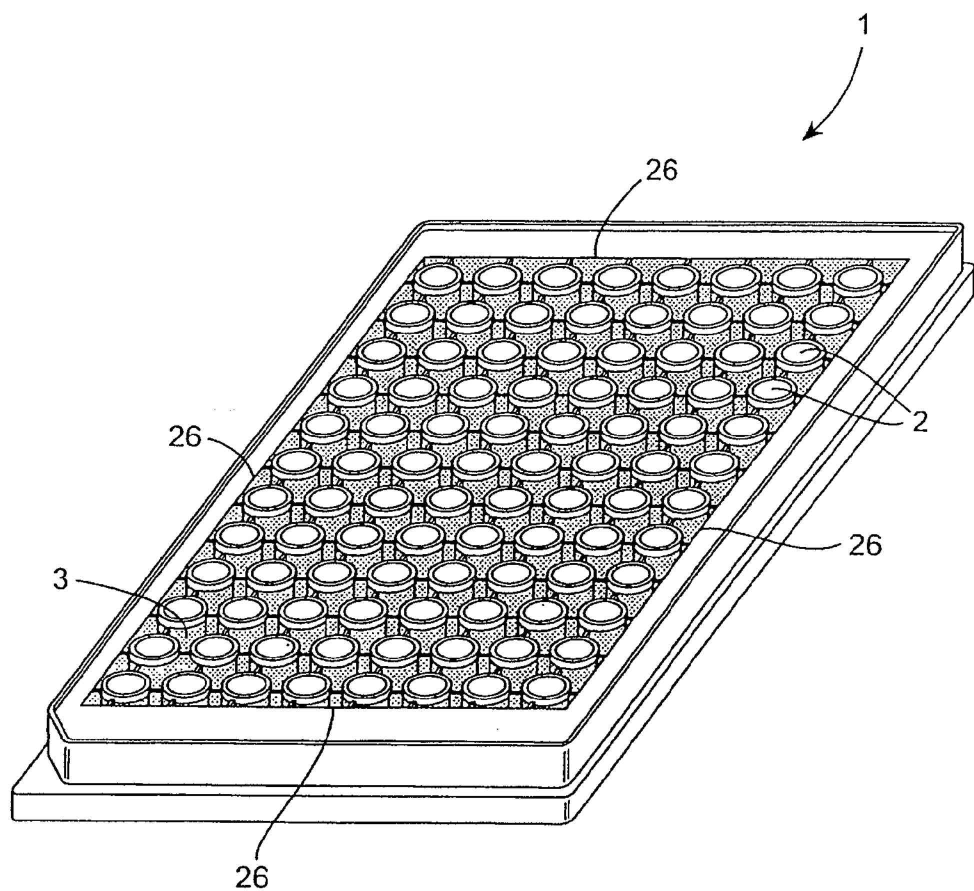
FIG. 3 is a perspective view of a multi-well plate according to the invention with a lid removed.
Figure 4:
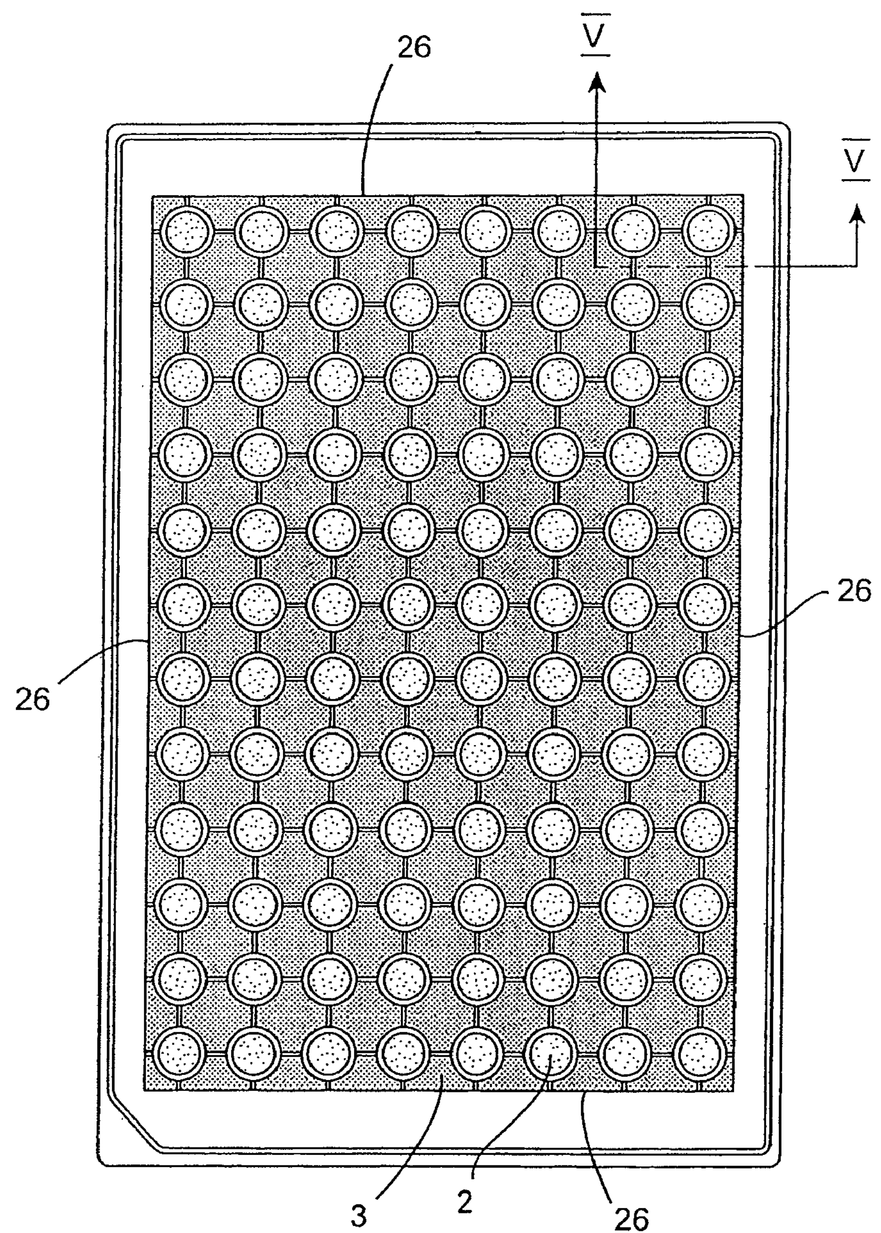
FIG. 4 is a top plan view of the multi-well plate of FIG. 3.
Figure 6:
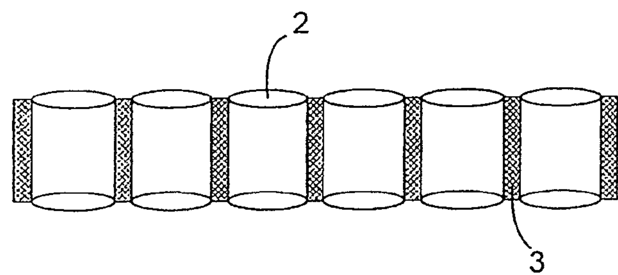
FIG. 6 is a schematic cross sectional view of part of a multi-well plate of the invention.
Figure 5:
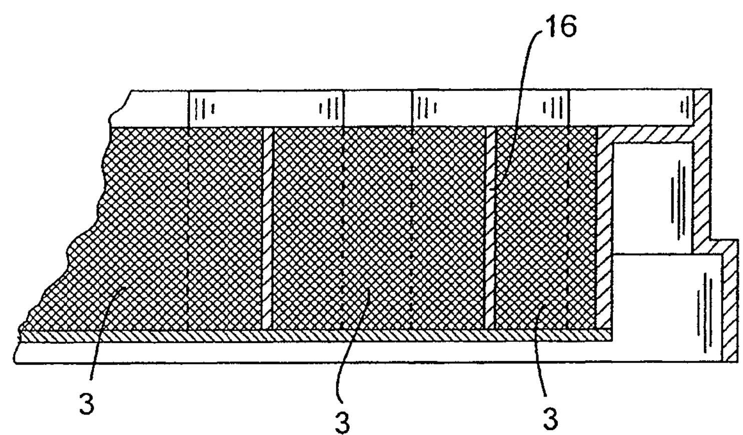
FIG. 5 is a cross sectional view on the line V-V in FIG. 4.

Referring to FIGS. 3 and 4, a multi-well plate 1 comprises a plurality of wells 2 which are surrounded by a substance 3 in accordance with the present invention. As shown in FIGS. 3 and 4 and more clearly in the cross sections of FIGS. 5 and 6, the substance 3 is located in the inter-well space. In certain circumstances, it may be preferably to have a large quantity of gel between the side walls 26 of the plate 1 and the wells 2 nearest to the side walls 26 of the plate 1 (peripheral wells) to further reduce the edge effect of the plate. Depending on the type of multi-well plate used, the substance 3 may also be located on the underside of a plate 1 in addition to the spaces between the wells and the space between the peripheral wells and side walls. Providing the substance on both the right side and the underside of a plate may give the plate a greater thermal insulation capacity. Alternatively, a multi-well plate may be specifically designed for example a multi-well plate having a larger than average channel between the peripheral wells and the side walls of the plate so that the channel can accommodate a larger amount of substance compared to conventional multi-well plates. The substance 3 in addition to occupying the space between the edge of the plate and peripheral wells 2 also at least partly surrounds the circumference of the wells 2. As can be seen in FIG. 5 in some embodiments of the multi-well plate 1, a partition 16 is formed by either a strengthening strut or a side wall of an adjacent well of the multi-well plate. The partition 16 prevents the substance 3 from surrounding the entire perimeter formed by the side walls of a well 2.

Figure 7:
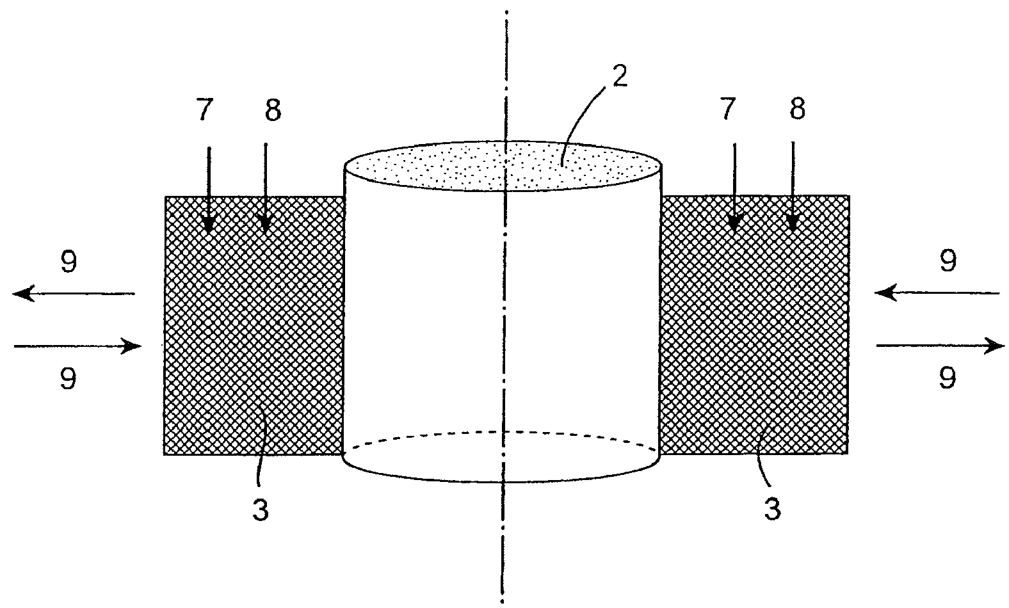
FIG. 7 is a schematic illustration of heat, gas and water transfer in a device of the invention when placed in an incubator.
Figure 8:
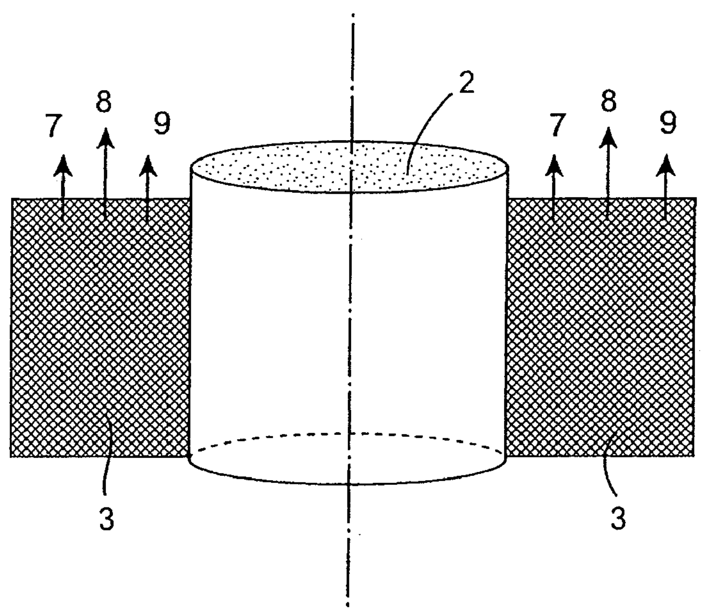
FIG. 8 is a schematic illustration of heat, gas and water transfer in a device of the invention when exposed to an external environment.

The schematic of FIGS. 7 and 8 show a well 2 of a multi-well plate surrounded by a substance of the invention. FIG. 7 illustrates the plate in an incubator set at about 37° C. and about 5% $CO_2$, thermal energy (illustrated by arrow 8) and $CO_2$ (illustrated by arrow 7) are absorbed by the substance 3. It is assumed that in the incubator water vapour between gel and saturated atmosphere of incubator is close to equilibrium with gel as indicated by arrows 9, this phase has been termed “loading”. FIG. 8 illustrates a plate removed from an incubator into open air or different environment, for example a laboratory bench, water vapour illustrated by arrow 9, $CO_2$ illustrated by arrow 7 and thermal energy illustrated by arrow 8 are released from the substance 3 down their respective concentration and physical gradients, hence replacing $CO_2$, water and heat which has been lost from a sample to the new experimental environment.

In a specific embodiment the device comprises a standard cell culture system wherein the wells of a multi-well plate are at least partly surrounded by a gel like substance. Alternatively the device may comprise wells for culturing cells wherein a portion of the wells comprise a matrix as described above. For example the matrix may be in fluid communication with the sample such that the matrix may act as donor. For example the matrix may allow two way communication between the sample and matrix for example for the passage of drugs, carbohydrates, chemokines, glucose, indicators, and the like.

In embodiments where the substance is on the side wall(s) of a well, or forms part of the side walls of a well, a margin will be required to prevent cells in a sample from migrating into the matrix. In one embodiment the top portion of the side walls of a well may comprise a substance. The sample (including cell culture medium) may be inserted into the well at a level below the substance side wall until it is desired to have the substance in fluid communication with the sample; at which point solution (such as culture medium) can be added to the well to raise the level of sample thereby bringing the sample into fluid communication with the substance.

Figure 13:
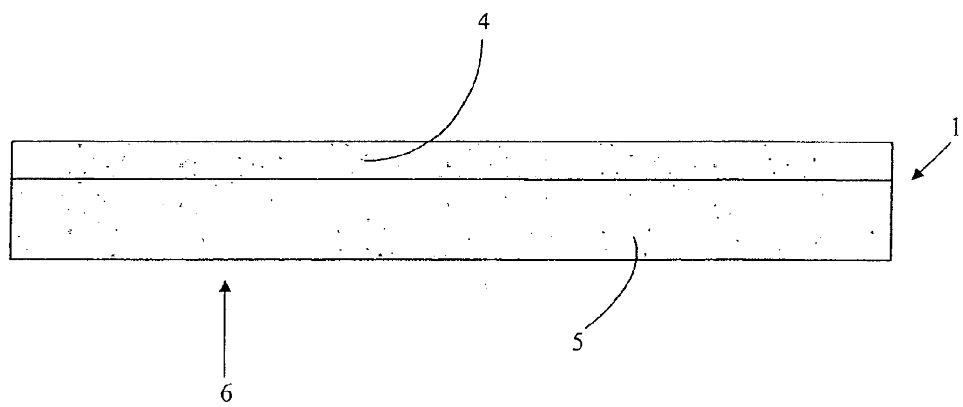
FIG. 13 is a side view of an insulated embodiment of a device of the invention.

In a further embodiment, the device may further comprise insulating material. In FIG. 13 the device incorporating a lid 4 of a sample retaining means is covered with a layer of insulating material. The insulating material may be polystyrene for example expanded polystyrene or the like. The body 5 of the sample retaining means 1 may also be covered with a layer of insulating material. Preferably the bottom 6 of the sample retaining means is free from insulating material so that, if required, the optical transparency of the sample retaining means 1 is retained. The addition of insulating material to the sample retaining means 1 may further improve the thermal insulation of the device. Typically, the insulating material may be a thin layer for example about 0.01 mm to about 10 mm thick. Desirably the insulating material is expanded polystyrene.

Figure 14:
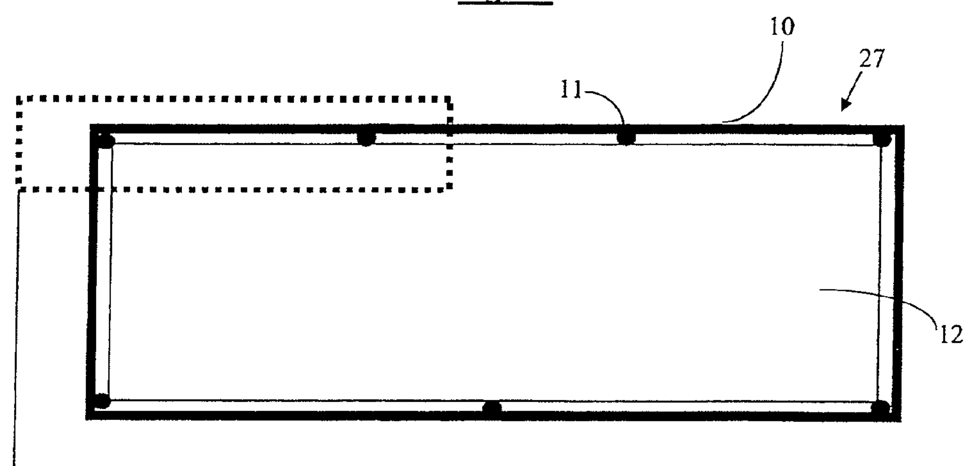
FIG. 14 is a plan view of an insulated lid of the invention.
Figure 15:
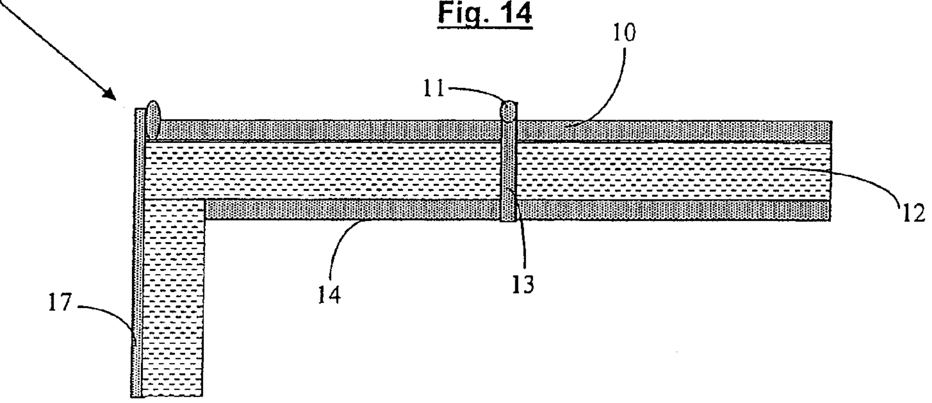
FIG. 15 is a cross sectional view of the lid of FIG. 14.

Referring to FIG. 14, in an alternative embodiment an insulated lid 27 may be provided. The insulated lid 27 comprises an outer lid support frame 10 comprising a plurality of locator points 11. As can be seen more clearly from FIG. 15, the outer lid support frame 10 is connected to an inner lid support frame 14 by a frame support brace 13. The insulating material 12 is located between the outer lid support frame 10 and the inner lid support frame 14. The outer lid support frame 10 further comprises a support brace 17 that is configured to extend down the side of a multi-well plate. The outer lid support frame 10, inner lid support frame 14 and support braces 13, 17 provide structural integrity to the insulated lid 27. The frame elements 10, 14, 17 are configured to surround the perimeter of a multi-well plate. The support braces 13, 17 provide additional strength to the insulated lid 27 and will assist in resisting tensile or compressive forces. The locator points 11 on the outer surface of the lid 27 assist in stacking plates on top of one another and are raised so as to provide a gap between the lid of a bottom plate and the base of the plate stacked on top of it. The lid 27 is configured to provide a substantially flat and mechanically stable surface which will rest on a multi-well plate to provide a gas permeable cover.

The invention will be more clearly understood from the following examples thereof.

EXAMPLES

Example 1

Matrix Composition (Agarose Gel)

The matrix was prepared by dissolving low melting point purified agarose in water to give a final concentrations of 1% agarose. The agarose solution was pipetted into the spaces surrounding the wells of a multi-well plate and allowed to solidify.

Example 2

Matrix Composition (Carbon Dioxide Maintainer/Stabiliser)

The matrix was prepared by dissolving low melting point purified agarose in a 0.044 M aqueous solution of sodium bicarbonate (3,700 mg per litre of sodium bicarbonate) to give a final concentrations of 1% agarose. The agarose solution was pipetted into the spaces surrounding the wells of a multi-well plate and allowed to solidify.

Example 3 pH Buffering Properties of Matrix pH was assessed by visual assessment of colour change of phenol red. Phenol red is used as a pH indicator in Dulbecco’s Modified Eagle’s Medium (DMEM) culture medium. When DMEM is placed in a properly calibrated incubator (5% $CO_2$ and 37° C.) the media should have a pH close to 7.4, under these conditions phenol red is red in colour. The pH of the media is maintained by interaction of the 5% $CO_2$ in the incubators atmosphere and sodium bi-carbonate in the DMEM (3700 mg/L). When the media is removed from the controlled atmosphere of an incubator, it tends to become more alkaline and will take on a mauve/purple appearance. It is this colour change which used to assess the effectiveness of the gel to buffer against changes in $CO_2$ out side of the tissue culture incubator.

Comparisons between phenol-red media in sample wells of a device containing a matrix in accordance with the invention (gel plates) and non-gel plates, revealed substantial differences in colouration. There was a marked colour change of phenol red in non-gel plates within 10 minutes of exposure to open lab environment. Whereas DMEM in the gel plates retained the same colour as the $CO_2$ incubator controls over the same time period.

We designed an experiment to demonstrate that retention of sample pH within the gel plates was due to the gels capacity to maintain CO, levels within the micro-plate environment, rather than that which maybe exerted by any thermal effects of the gel. In this experiment we warmed both gel and normal plates to a temperature of 37° C. at normal atmospheric CO, levels and then compared these plates with those which had been maintained at room temperature and normal atmospheric $CO_2$ for two hours (where pH had increased). Our observations revealed that there was no difference in colour between heated plates and those at room temperature.

To further demonstrate that sample liquid pH was buffered by $CO_2$ in gel plates we introduced $CO_2$ gas back into the gel and non-gel plates whilst still maintaining them at room temperature. This procedure resulted in a restoration of the sample liquid colour close to that seen when plates were maintained in a 5% $CO_2$ incubator.

Example 4

Temperature Retention (Matrix)

Wells of normal and matrix treated 96 well plates (a device in accordance with the present invention) were pre-filled with 200 μl saline solution prior to maintenance in a standard tissue culture incubator (set at 37° C., 95% air and 5% $CO_2$) for 12 hours. Prior to initiation of experimental protocol, temperature measurements of liquid well contents were recorded. Plates were then transferred from the incubator to standard laboratory conditions where room temperature was maintained at 19° C. Measurements in corresponding upper, medial and lower central wells of 96 well plates were recorded at times indicated. Data shown is expressed as percentage, where 100% represents starting temperature and 0% corresponds to room temperature (i.e. extremes of dynamic range of thermal conditions of experiment). (FIG. 9)

Figure 9:
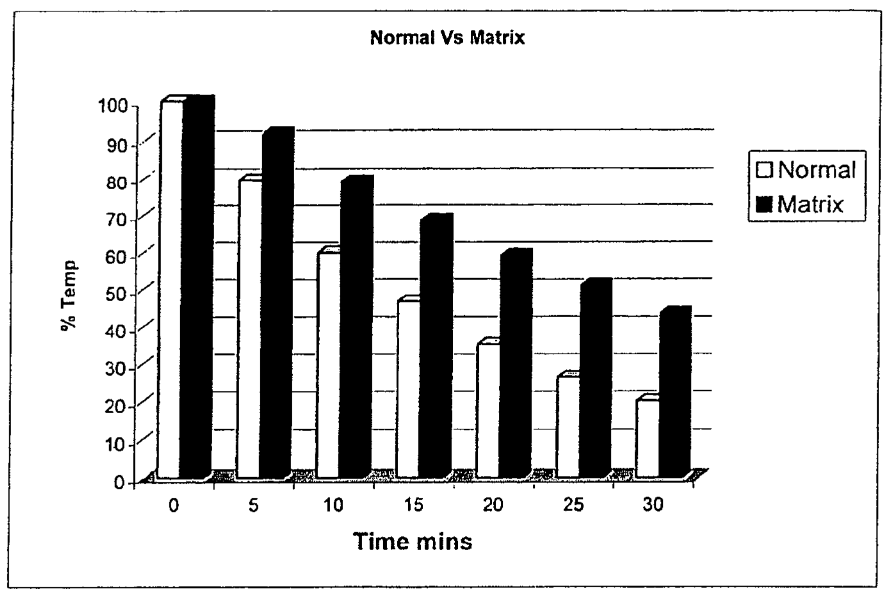
FIG. 9 is a bar chart showing the temperature retention of a matrix of the invention over time.

As can be seen from FIG. 9, Time (in minutes) is along the x axis and percentage temperature is along the y axis. At time zero, both the normal plate (white bar) and plate containing matrix (black bar) have 100% temperature. As the time in which the plates are left at room temperature (19° C.) increases, the percentage temperature decreases. After 10 minutes, the normal plate has 45% drop in temperature while at 30 minutes the plate containing matrix temperature has dropped only 12% of the starting temperature. In contrast the plate containing matrix has a 20% decrease in temperature while at 30 minutes the temperature is 35% of the starting temperature. Changes in temperature occur over a longer period, in plates containing matrix compared to normal plates. These gradual thermal changes are likely to do less harm to samples, for example, cells, than the rapid changes, in temperature observed in normal plates.

Example 5

Rate of Re-Warming

Wells of normal and matrix treated 96 well plates were pre-filled with 200 μl saline solution and pre-warmed to a temperature of 37° C. and then maintained at room temperature for 30 minutes. Temperature measurements of liquid well contents were then recorded. Plates were then transferred into an incubator (set at 37° C., 95% air, 5% $CO_2$). Measurements in corresponding upper, medial and lower central wells of 96 well plates were recorded at 30 minutes. These data are expressed as temperature rise (° C. per minute) (FIG. 10).

Figure 10:
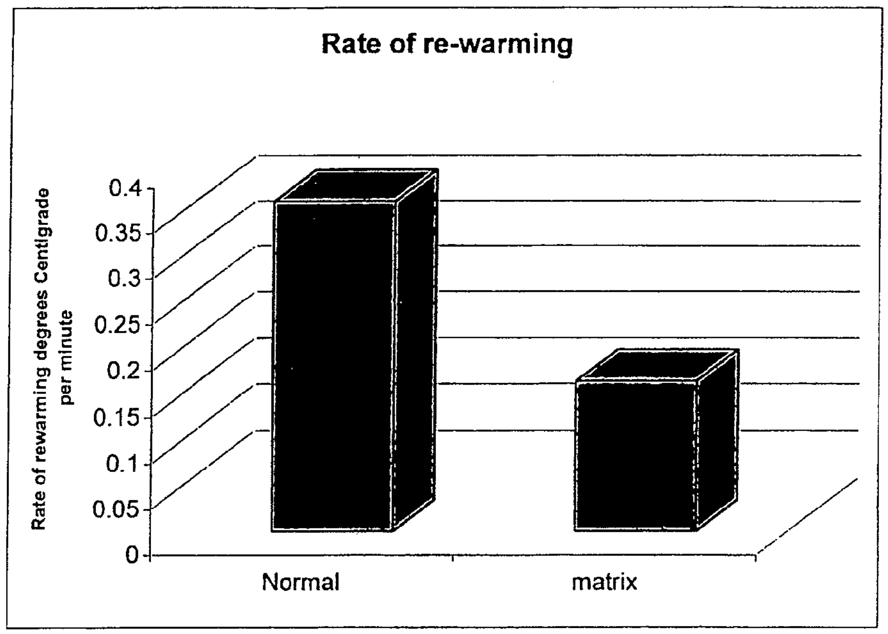
FIG. 10 is a bar chart showing the rate of the re-warming of a matrix of the invention.

FIG. 10 demonstrates that rate of warming of plates containing matrix is slower compared with the rates of warming normal plates.

The data of FIGS. 9 and 10 when taken together illustrate that when a matrix plate is taken from one environment, to another where there is a temperature differential between the two environments, for example, from an incubator to an open laboratory, or from a freezer to an open laboratory. The temperature of the matrix plate remains more constant than the temperature of normal plates. Hence, contents of wells of matrix plates are subject to smaller fluctuations in temperature, therefore reducing the possible harmful effects of large temperature fluctuations.

Example 6

Cell Growth

Wells of normal and matrix treated 96 well plates were seeded at equal density (3000 cells per well) with cells of immortalised cell line THP1 prior to maintenance in a standard tissue culture incubator (set at 37° C., 95% air, 5% $CO_2$) for 48 hours. Both matrix and normal plates were placed in middle of the incubator side by side.

Figure 11:
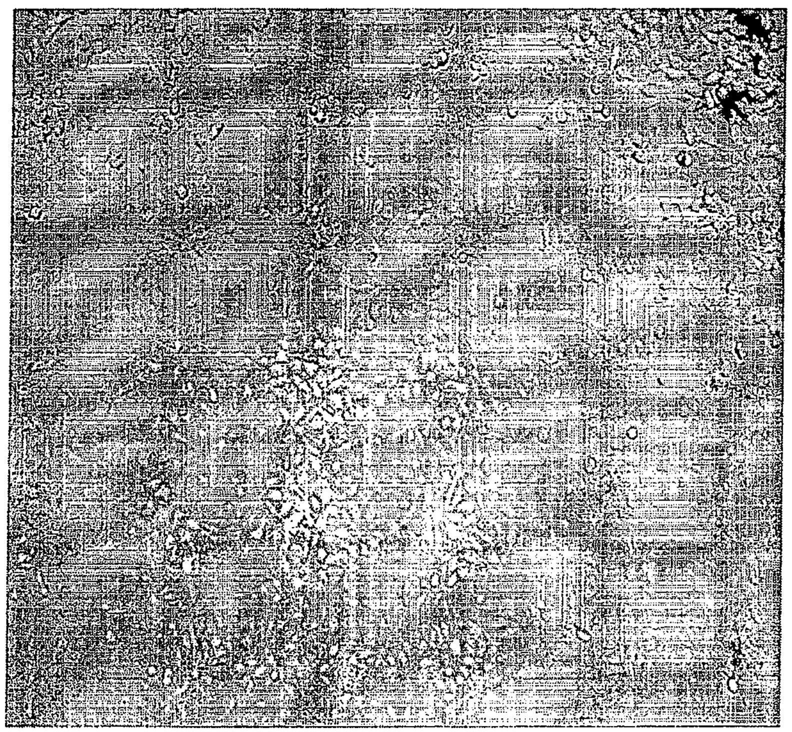
FIG. 11 is a photograph of THP1 cells growing in a well of a device of the invention.
Figure 12:
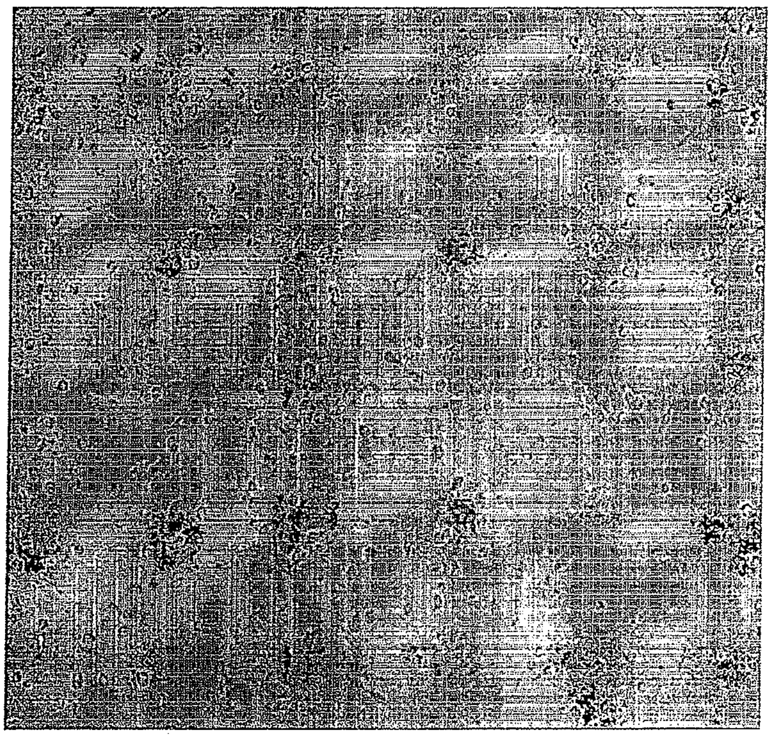
FIG. 12 is a photograph of THP1 cells growing in a well of a standard 96-well plate.

As can be seen from FIGS. 11 and 12 cells reach confluency faster in the matrix plates (FIG. 11) and the cells appear to be more viable than cells grown in a normal 96 well plate (FIG. 12), these results were also reflected in plates which were half matrix and half normal, the cells grew more quickly in the matrix half (not shown). This is possibly due to the fact that the micro environment is more stable in the matrix plates than the normal ones.

It was also noted that by visual inspection of phenol red colour change that pH changes in the medium contained in the matrix plates remained unchanged for periods of up to 30 minutes, whereas substantial changes were noted in normal plates.

Example 7

Temperature Retention (Matrix and Insulation)

Wells of normal and gel and insulated 96-well plates were pre-filled with 200 μl saline solution prior to maintenance in a standard tissue culture incubator (set at 37° C., 95% air/5% $CO_2$) for 12 hours. Prior to initiation of experimental protocol, temperature measurements of liquid well contents were recorded. Plates were then transferred from the incubator to standard laboratory conditions where room temperature was maintained at 19° C. Measurements in corresponding upper, medial and lower central wells of 96-well plates were recorded at times indicated. Data shown is expressed as percentage temperature, where 100% represents starting temperature and 0% corresponds to room temperature (i.e. extremes of dynamic range of thermal conditions of experiment).

Figure 16:
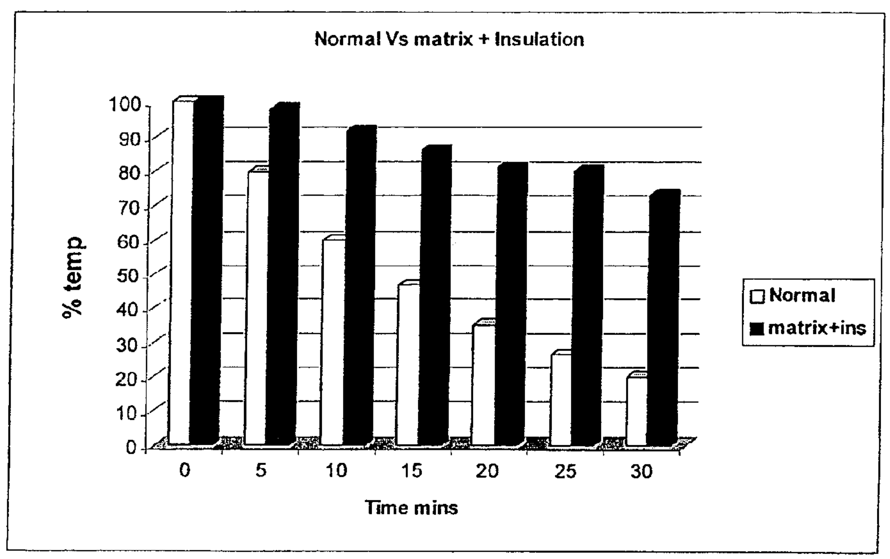
FIG. 16 is a bar chart showing the temperature retention of a device of FIG. 13.

As can be seen from FIG. 16, 96-well plates containing matrix and insulation (black bar) retain temperature for longer than 96-well plates without matrix and insulation (white bar).

Example 8

Evaporation and Moisture Edge Effects

Figure 17:
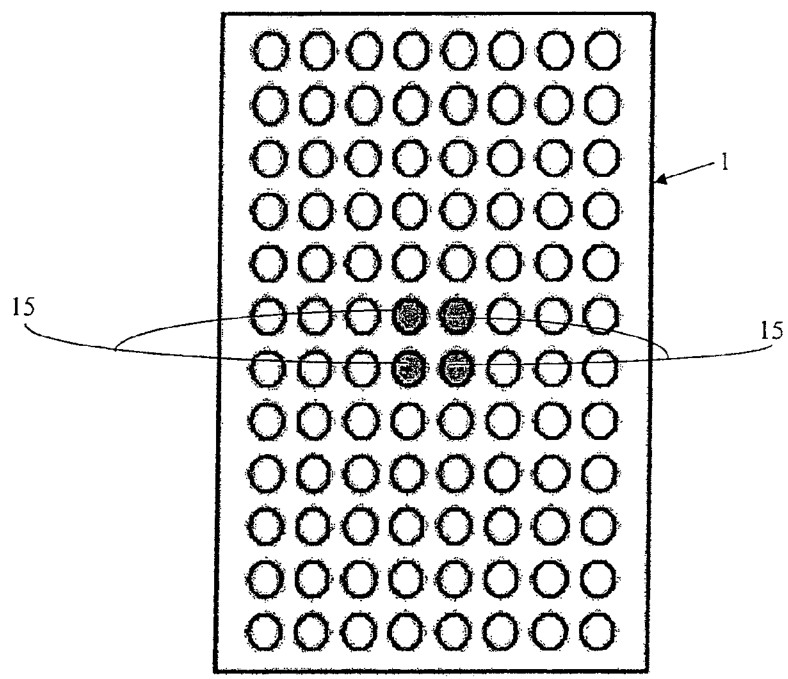
FIG. 17 is a schematic illustration of the wells used for the measurements of FIG. 18.
Figure 18:
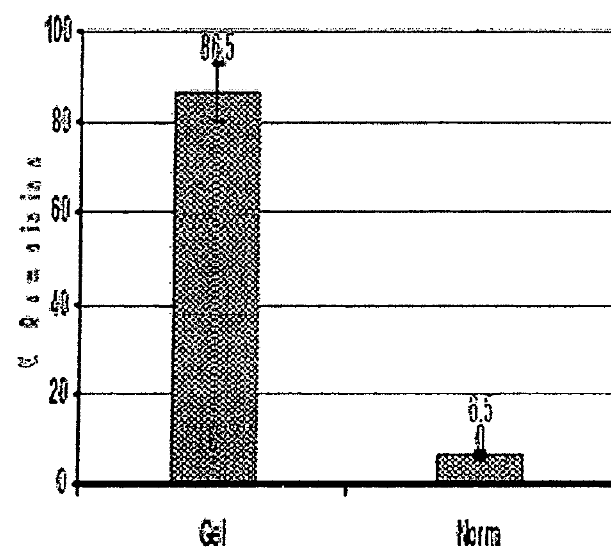
FIG. 18 is a bar chart illustrating the water retention properties of a device of the invention.

This experiment was designed to determine the water retention properties of sample in a well of a gel plate in accordance with the invention compared to a sample in a well of a non-gel plate. Wells of 96 welled plates were filled with 200 μl serum free culture medium and maintained in a standard tissue culture incubator for 84 days. The wells 15 indicated in FIG. 17 were used as sample wells in this experiment. Referring to FIG. 18 it can be seen that sample wells of the gel plate had a greater than 13 fold water retention property compared to non-gel plates (data represent n=4 experiments of percentage volume remaining after incubation time).

Example 9

Evaporation and Moisture Edge Effects

Figure 19:
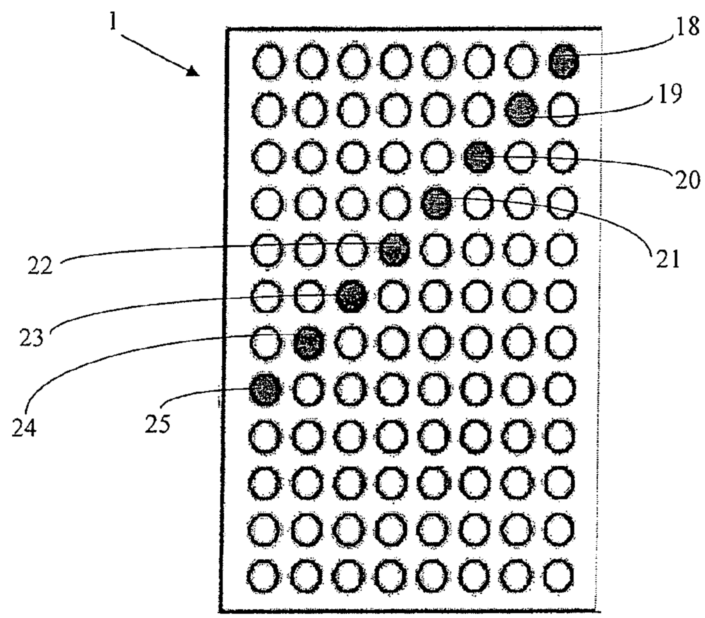
FIG. 19 is a schematic illustration of the wells used for the measurements of FIG. 20.
Figure 20:
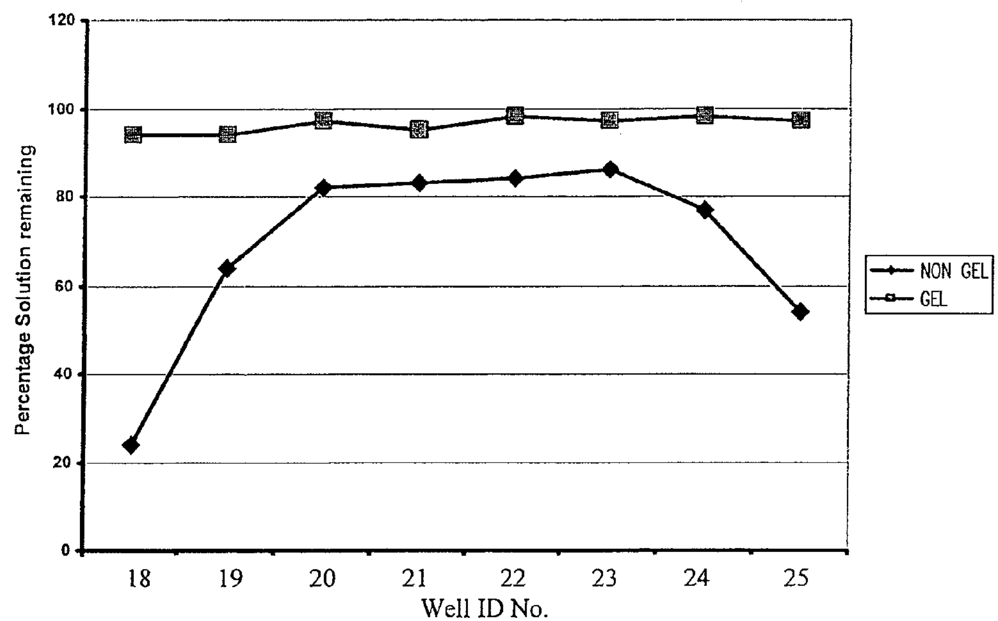
FIG. 20 is a graph illustrating the water retention properties of a device of the invention.

This experiment was designed to determine the water retention properties of sample in a well of a gel plate in accordance with the invention compared to a sample in a well of a non-gel plate. Wells of 96 welled plates were filled with 100 μl serum free culture medium and maintained in a standard drying oven set at 50° C. for a duration of 48 hours. The wells 18, 19, 20, 21, 22, 23, 24, 25 indicated in FIG. 19 were used as sample wells in this experiment. As can be seen from FIG. 20, the gel plates retained between 94 and 98% of moisture in wells compared to 24 to 91% in non-gel plate wells. The moisture retained in the gel plate wells was fairly consistent for all wells 18, 19, 20, 21, 22, 23, 24, 25 tested whereas in the non-gel plates the outer most wells 18 and 25 had a significant loss of fluid demonstrating the edge effect of standard multi-well plates.

Referring to FIGS. 21 to 27, a lid in accordance with the invention has two co-operating portions 52 and 53. Portion 52 can be considered to be the upper (outer) lid whereas portion 53 can be considered to be the lower (inner) lid. Each of the portions 52 and 53 comprise at least one orifice 54 and 57 respectively. The number of orifices 54, 57 will be complimentary to the number of wells in the multi-well plate on which the lid is to be used. For example, if a 96-well plate is used the portions 52 and 53 of the lid will have 96 orifices 54, 57. The orifices 54, 57 of the lid may be positioned so that they will be complimentary, such as directly over, the wells in the multi-well plate when the lid is fitted over the plate correctly. The width (diameter) of the orifices 54, 57 is between about 1 to about 5 mm. Desirably, the orifices 54, 57 will be of suitable size and shape (dimensions) to receive an injection from an automated culture or HTS and/or robotic handling system.

Figure 21:
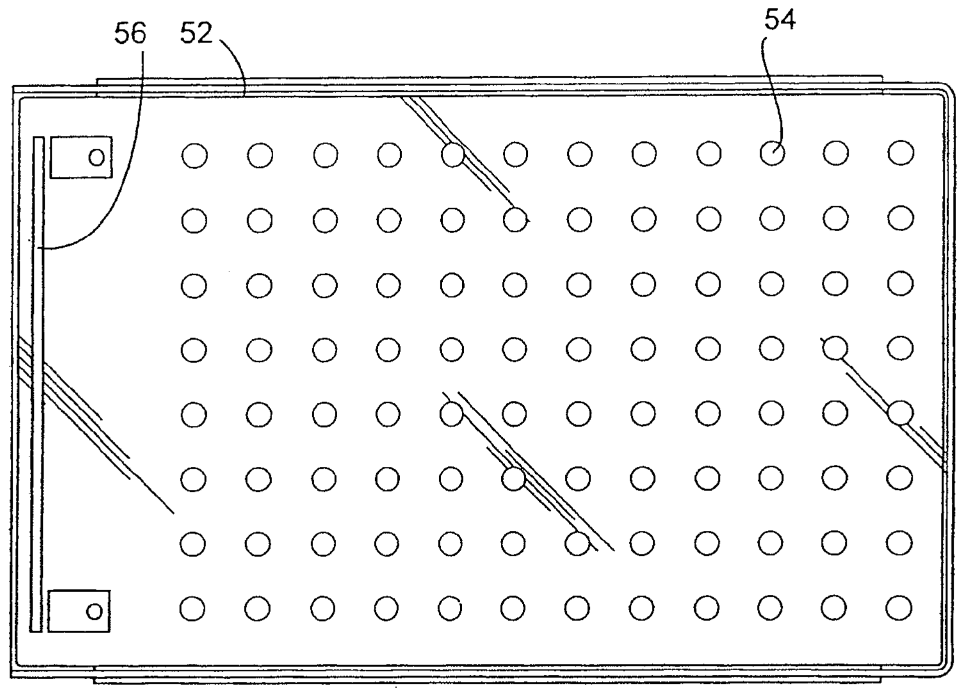
FIG. 21 is a top plan view of an upper lid portion.
Figure 22:
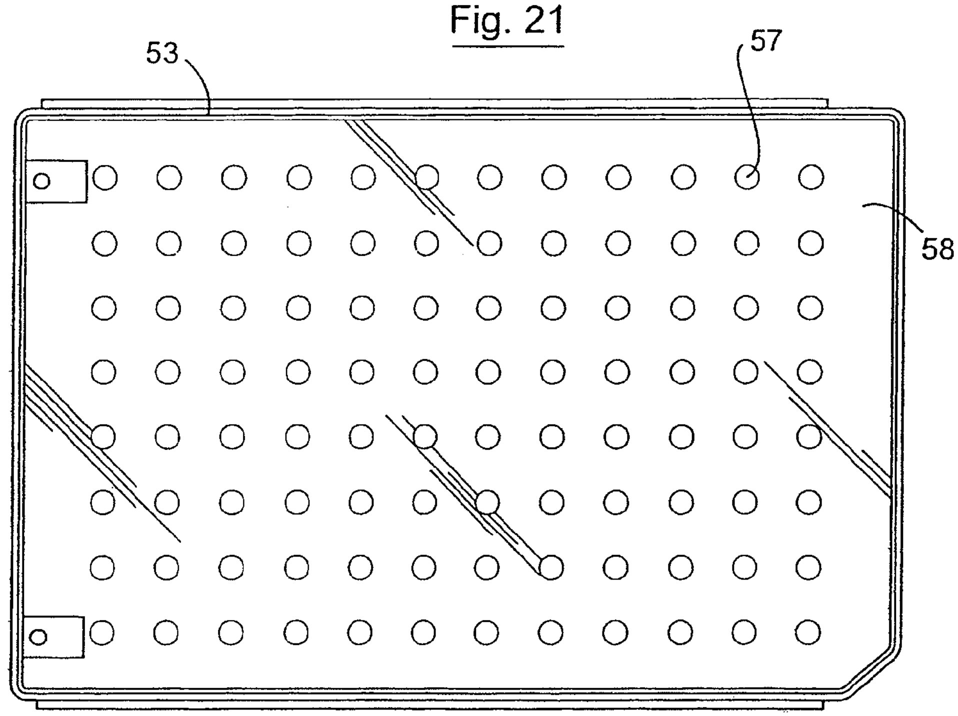
FIG. 22 is a top plan view of a lower lid portion configured to correspond with the upper lid portion of FIG. 21.

Referring to FIGS. 21 and 22, a lid in accordance with the invention comprises an upper lid portion 52 (FIG. 21) having a plurality of orifices 54 that extend through the outer lid portion 52, and a portion 56 which provides a means for assisting in the opening and/or closing of the lid. The lid further comprises a lower lid portion 53 (FIG. 22) which has a plurality of orifices 57 extending through the inner lid portion 53. The orifices 53 are surrounded by an area 58 that can be considered as a spacer region.

The orifices 54, 57 pass through the lid portions 52 and 53 such that when the lid is in the "open" configuration, a channel is formed through the lid providing access to the interior of a well on a plate in which the lid is positioned. When the lid is in the "closed" position, the channel formed by substantial alignment of orifices 54 and 57 is closed by misalignment of the orifices 54 and 57 or by insertion of a closing means that functions to block fluid communication of the orifices 54 and 57. In one embodiment, orifices 54 and 57 are substantially circular and have a diameter significantly smaller than the diameter of a well of a multi-well plate. Typically a well of a 96 well multi-well plate has a diameter of about 7 mm, the diameter of the orifices 54 and 57 may be about 3 mm.

The difference in size between the wells of the multi-well sample plate and the orifices 54 and 57 may allow the channel formed by alignment of orifices 54 and 57 to be closed by misaligning the orifices for example by moving the outer portion 52 with respect to the inner portion 53 or vice versa. In such a configuration, the inner portion 53 acts as a barrier to the orifices 54 in the outer portion 52 and vice versa (orifice 54 overlaps spacer region 58).

The orifices 54 and 57 may be of different sizes and shapes but may preferably be the same size and shape.

The spacer region 58 may be a continuous row or column, containing at least one opening 57. Alternatively, the spacer region 58 is discontinuous such that each opening 57 has an individual spacer region 58 associated with it. In one embodiment it may be desirable that the opening 57 may be located (situated) near the border of the spacer region 58. Alternatively, the opening 57 may be located towards the border of the spacer region 58 so that there is a sufficient area of spacer region 58 to act as a closure for opening 54 in the outer lid portion 52 when the lid is in a closed position. Whilst the spacer region 58 has been described as being located on (with) the openings 57 of the inner portion 53, the spacer region 58 may alternatively be associated with the outer portion 52.

Desirably, the spacer region 58 is raised in profile. For example, the spacer region 58 may extend from a face of the inner 53 or outer 52 lid portions. Typically, the spacer region will have a height of from about 0.5 to about 5.0 mm. When the spacer region 58 is raised, it may function to reduce the surface to surface contact between the inner 53 and the outer 52 lid portions which may result in a decrease in the amount of friction caused by the portions 52, 53 moving with respect to one another. The spacer region 58 may also function to prevent unwanted matter such as liquids, condensation or solid particulate matter, for example dust particles or the like, from entering the space between the inner 53 and outer 52 portions. The spacer region 58 may also limit or restrict unwanted capillary effects between the lid portions 52, 53 that may cause the two portions to stick together, for example condensation. Whilst the spacer region 58 has been described with reference to the openings or orifices 54 and 57, the spacer region 58 may be located anywhere in or on the lid so long as the spacer region 58 provides the functions outlined above.

The orifice 57 may be positioned near the boundary of the spacer region 58 such that when the orifices 54 and 57 are misaligned (closed configuration) the spacer region 58 closes access of a well of a multi-well plate to the external environment.

In a further embodiment (not shown) the openings 54 and 57 in the outer portion 52 and inner portion 53 may be staggered or arranged in such a way so as to permit access to specific wells or rows of wells or columns of wells depending on the orientation and/or position the lid is moved in.

As it is sometimes necessary to add or remove liquids from different regions of a well of a sample plate for example the middle or the outer edge of the well, the opening 57 of the inner portion 53 may be substantially rectangular in shape and configured such that the length of opening 57 corresponds to a key dimension of the well, such as the radius or the diameter, for example, the opening 57 only provides access to the top edge, bottom edge, middle, left edge or right edge of a well when the lid is open.

Figure 23:
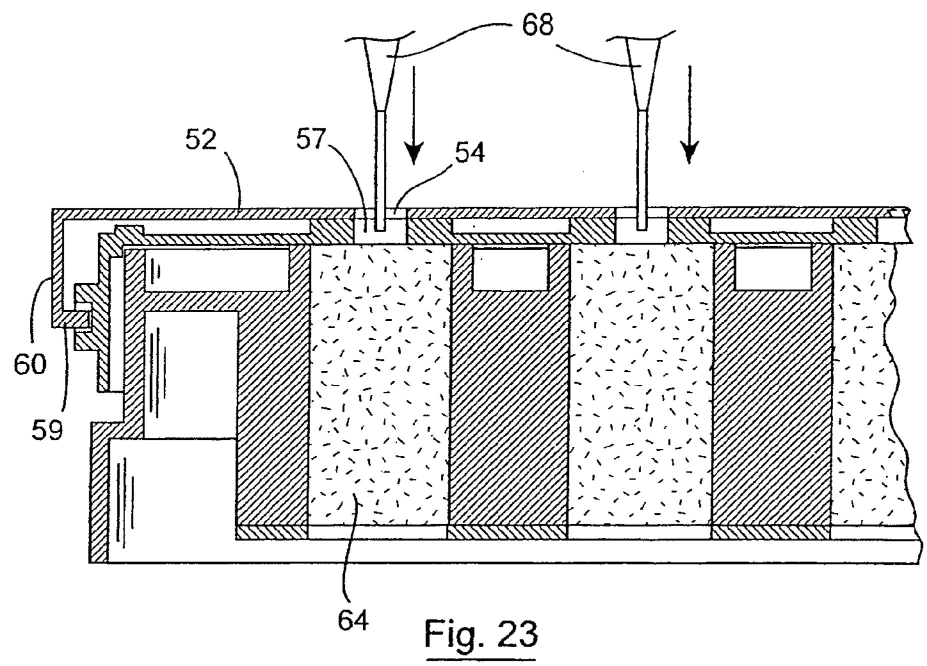
FIG. 23 is a cross sectional view of a lid of the invention in the open configuration.
Figure 24:
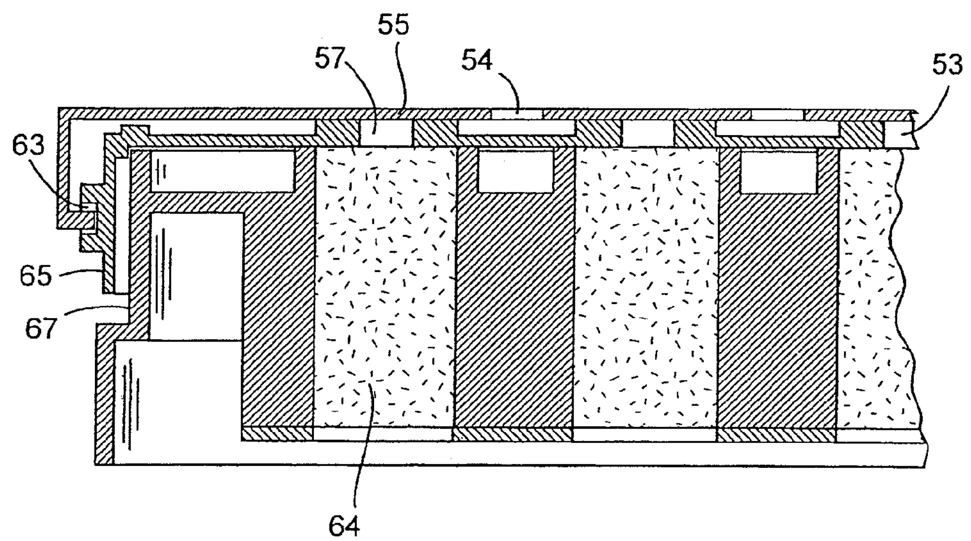
FIG. 24 is a cross sectional view of a lid of the invention in the closed configuration.

Looking at FIGS. 23 and 24, the outer portion 52 has a means for attaching the outer portion 52 and the inner portion 53 together. In the embodiment shown, the attachment means comprise a projection 59. In the embodiment shown, the projection 59 is integral with side wall 60 of the outer portion 52.

In one embodiment, outer portion 52 has a plate-like portion comprising orifices 54. A side wall 60 extends from the plate like portion, the side wall 60 terminating in a projection 59 at its free end. The outer portion 52 may also comprise a mirror-image side wall extending from the opposite side of the plate-like portion (not shown). In one respect the outer portion may be considered as substantially square bracket shaped, having inturned flanges at its free ends.

The inner portion 53 may have a groove 62 designed to accommodate/co-operate with the projection 59 of the outer portion 52 (e.g. tongue and groove arrangement). Desirably, the inner portion 53 may also have a side wall 65 to engage with a multi-well or single-well sample plate. The side wall 65 may be a continuous side wall along the entire perimeter of inner portion 53. Alternatively side wall 65 may comprise a number of portions to enable the inner portion 53 to co-operate with a sample plate so that the lid is retained on the sample plate.

FIGS. 23 and 24 show the lid positioned on a multi-well sample plate. The side wall 65 of the inner portion 53 is in contact with the side wall 67 of the sample plate, thereby retaining the lid on the sample plate. In addition, the side wall 60 may also act as a stop to prevent the outer portion 52 from moving too much with respect to the inner portion 53. Alternatively, the inner portion 53 may be secured on the sample plate (not shown).

The portions 52 and 53 may be linked such that portion 52 may move relative to portion 53 and vice versa. Desirably the portions 52 and 53 move in a linear plane relative to one another. Preferably, the portions 52 and 53 slide relative to one another. Preferably the lid also has at least one stop (not shown). The stop may limit the amount of travel of portion 52 with respect to portion 53. Desirably, the length of travel of portion 52 with respect to portion 53 will be between about 1 to about 5 mm. However in alternative embodiments (not shown) the portions 52 and 53 may pivot relative to one another. In the open configuration of FIG. 23, the orifices 54 and 57 are aligned. Such as the orifices 54 and 57 are on top of one another. In the open configuration the aligned orifices define a conduit through the lid through which a pipette 68 can pass in the direction of the arrows. In FIG. 23 the orifices 54 and 57 are shown as being fully aligned however in some situations it will be desirable to have a conduit defined by off-set orifices 54 and 57 (not shown) to reduce the width of the conduit. When the orifices 54 and 57 are off-set to form a channel, the entire surface of a well 64 of a plate will not be exposed to the external environment, rather only a portion of the well will be exposed. In the open or partially open configuration, the conduit defined by the orifices 54 and 57 provide a means for entry into the wells of a plate. When the wells of a plate are exposed (fully or partially) samples, solutions and the like can be aspirated or dispensed into the wells. In the closed configuration of the lid (FIG. 24) portions 52 and 53 are off-set relative to one another such that a solid portion 55 of portion 52 covers the inner opening of orifices 57 of portion 53 and vice versa. When the lid is positioned on a plate and the inner portion of the orifices 57 are covered by the solid portion 55 of the complimentary member, the wells of the plate are protected from the external environment.

In an alternative embodiment, portions 52 or 53 may comprise a number of movable members. In such an embodiment the movable members can be operated independently of one another. For example only the wells of a selected row or column may be exposed at any given time.

A plate with the lid described above may also be used, for example, in automated tissue culture systems or robotic liquid handling systems and the like.

Figure 25:
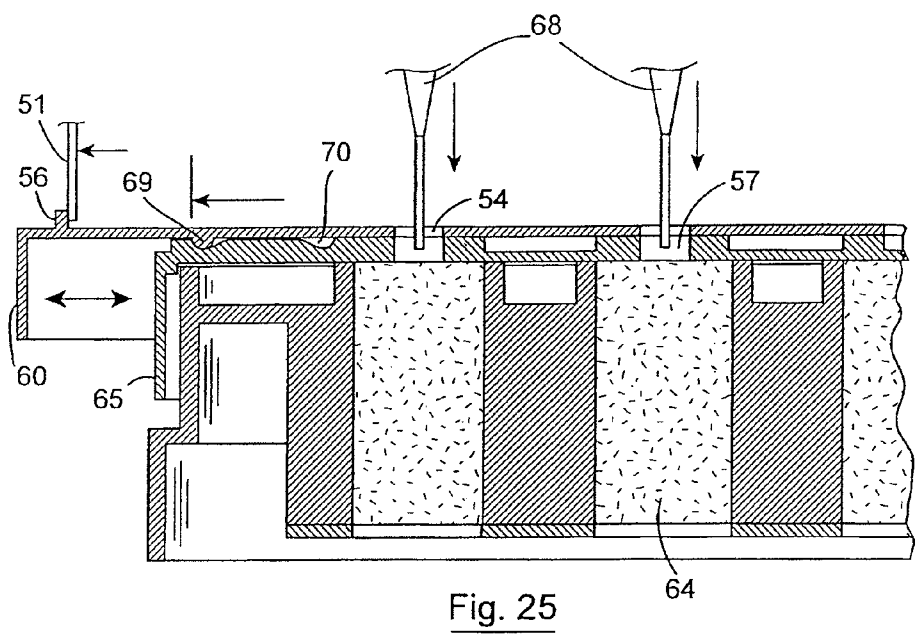
FIG. 25 is a cross sectional view of an alternative embodiment of a lid of the invention in an open configuration.

Referring to FIG. 25, the outer portion 52 may also have an area/portion such as a projection 56 to assist in moving the outer portion 52 with respect to the inner portion 53. The inner portion 53 may have more than one projection 56. The lid may be configured to allow an automated machine (such for example, as an automated liquid handler or a HTS machine) to open the lid of a plate and gain access to the interior of a well 64.

Referring to FIG. 25 a needle, pipette tip or probe 51 of an automated device locates a projection 56 on the closed lid. The probe 51 pushes against the projection 56 causing the outer portion 52 to slide relative to the inner portion 53 in the direction of the arrow. When the lid is open, an automated device pipette 68 may dispense or aspirate liquid into or out of the well 64. The portion of the automated device used to move the lid may also be used to dispense/aspirate liquid from the well 64. However in alternative embodiments, the lid may be opened by a separate means 51 of the automated device and the pipette 68 may only aspirate or dispense liquid. This embodiment will be preferred if aseptic techniques of aspiration and/or dispensing are required.

Figure 26:
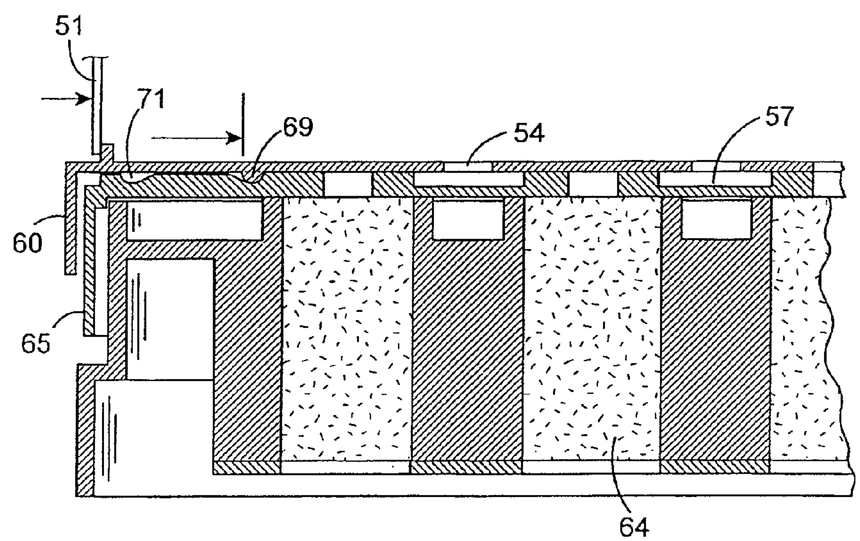
FIG. 26 is a cross sectional view of an alternative embodiment of a lid of the invention in a closed configuration.

In FIG. 26, the lid is closed by pushing against projection 56 in the direction of the arrow. The dispensing device 68 may be used to close the lid. Alternatively, a different part of the automated device 51 may be used to close the lid.

It will be appreciated that the projection 56 can also be used to manually open and close the lid.

In an alternative embodiment (not shown) the area/portion of the outer lid 53 used to assist in opening and closing of the device may be a button or ridge or depression or the like. Generally, the area/portion will be designed so that The wells of a sample plate can be accessed without the automated device or end user having to remove the entire lid of a sample plate. In addition, the lid may also comprise a biasing means to bias the moveable lid portion in a closed position. Preferably the biasing means is a spring or the like.

Figure 27:
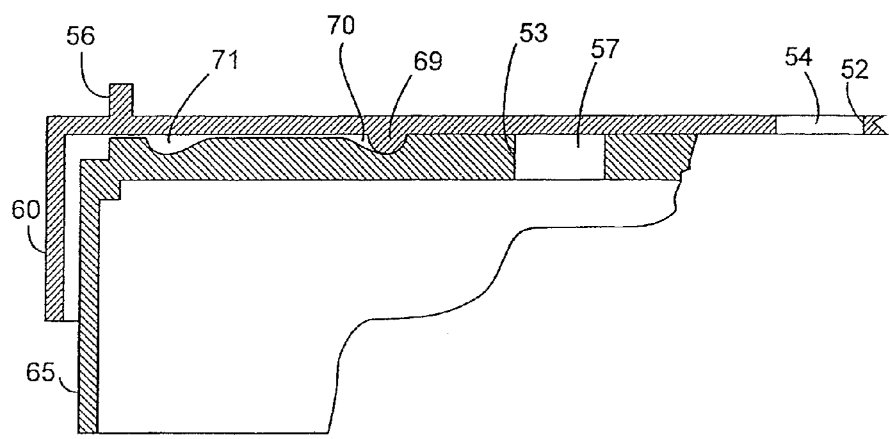
FIG. 27 is an exploded view of the lock mechanism of the lid of FIGS. 25 and 26.

The lid may also comprise a lock such as the one illustrated in FIGS. 25 to 27. The lock 69 may be located on the moveable portion of the lid 52, and the non-moveable portion of the lid 53 may be designed to have a lock cooperating portion 70, or vice versa. Desirably, the lock 69 may compliment the movement of the outer portion 52 with respect to the inner portion 53. The arrow in FIG. 25 indicates direction of movement of the outer lid 52 when the lid is in the open configuration.

FIG. 26 shows the lock 69 moving towards the closed configuration. The direction of movement is illustrated by the arrow. In the embodiment shown, the lock 69 is a slider that can be engaged when the lid is slid between the open and closed configuration. The inner portion 53 may also comprise an inclined groove 71 for housing the lock 69 when the lid is in the open configuration (FIG. 25). The locking mechanism may prevent unwanted or accidental opening of the lid when the sample plate is being transported. In particular, the locking mechanism may stabilise the lid if a number of sample plates are stacked one on top of each other.

The lid may be constructed of a plastics material for example a polyester or a polyamide, an epolyvinylchloride, a polystyrene or the like. Preferably, the lid will be constructed from the same material as the sample plate.

The lid of the invention may be used in combination with a device 1 described above.

The invention is not limited to the embodiments hereinbefore described which may be varied in detail.

The invention claimed is:

1. A multi-well plate for housing a sample comprising a plurality of sample wells arranged to form inter-well spaces and a space between side walls defining the multi-well plate and sample wells nearest to the side walls, and an aqueous gel like material onboard buffering substance wherein the onboard buffering substance is located in the inter-well spaces and in the space between side walls defining the multi-well plate and sample wells nearest to the side walls.

2. The multi-well plate as claimed in claim 1, wherein the sample is one or more selected from the group comprising: biological, chemical, physical, biochemical, and nanotechnical.

3. The multi-well plate as claimed in claim 1 wherein the substance is solid or semi-solid at room temperature.

4. The multi-well plate as claimed in claim 1 wherein the substance is selected from: a natural gel-like material, a synthetic gel-like material, or a semi-synthetic gel-like material.

5. The multi-well plate as claimed in claim 1 wherein the substance is a polymer.

6. The multi-well plate as claimed in claim 1 wherein the substance comprises one or more selected from the group consisting of agar, agarose, acrylamide and gelatine.

7. The multi-well plate as claimed in claim 1 wherein the substance further comprises one or more additive selected from the group consisting of oxygen scavengers, exothermic compounds, endothermic compounds, pH indicators, dyes, carbon dioxide maintainers/stabilizers, oxygen maintainers/stabilizers, nitrogen maintainers/stabilizers, antioxidants, carbon sources, infection indicators and anti-microbial agents.

8. The multi-well plate as claimed in claim 1 wherein the onboard buffering system substance is a thermal buffer.

9. The multi-well plate as claimed in claim 1 further comprising a lid, the lid may be moveable to allow access to the sample retaining means.

10. The multi-well plate as claimed in claim 1 further comprising insulating means, the insulating means may be a layer of insulating material, the insulating means may be polystyrene, the insulating means may be a lid.

11. The multi-well plate as claimed in claim 1 wherein the onboard buffering substance is an atmospheric buffer.

12. The multi-well plate as claimed in claim 7 wherein the additive is an oxygen scavenger, and wherein the oxygen scavenger is selected from one or more of the group consisting of: sulphite, catalase, carnosine, N-acetylcarnosine, homocarnosine, carbohydrazide, oxygen scavenging enxymes and pyrogalol.

13. The multi-well plate as claimed in claim 7 wherein the additive is an exothermic compound, and wherein the exothermic compound is selected from one or both of: sodium hydroxide and hydrochloric acid; glycine (glycerol) and lower polyglycols.

14. The multi-well plate as claimed in claim 7 wherein the additive is an endothermic compound, and wherein the endothermic compound is selected from one or both of: sodium hydroxide and water; citric acid and sodium hydroxide.

15. The multi-well plate as claimed in claim 7 wherein the additive is a pH indicator, and wherein the pH indicator is phenol red.

16. The multi-well plate as claimed in claim 7 wherein the additive is a dye, and wherein the dye is selected from the group consisting of: Remazol Brilliant Blue R (RBBR), poly R-478, guaiacol and tannic acid.

17. The multi-well plate as claimed in claim 7 wherein the additive is carbon dioxide maintainer/stabilizer, and wherein the carbon dioxide maintainer/stabilizer is selected from bicarbonate of soda or soda lime.

18. The multi-well plate as claimed in claim 7 wherein the additive is a carbon source, and wherein the carbon source is selected from one or more of the group consisting of: glucose, lactose, and sucrose.

19. The multi-well plate as claimed in claim 7 wherein the additive is an infection indicator, and wherein the infection indicator is a chemical inhibitor of microbial growth such as citric acid and bromothymol blue.

20. The multi-well plate as claimed in claim 7 wherein the additive is an antimicrobial agent, and wherein the antimicrobial agent is selected from one or more of: bacteriocidals, antibiotics, and fungicidals.

21. The multi-well plate as claimed in claim 5 wherein the polymer has a weight/volume (w/v) percentage concentration of between about 0.1% to about 10%.

22. The multi-well plate as claimed in claim 5 wherein the polymer has a weight/volume (w/v) percentage concentration of between about 0.1% to about 5%.

23. The multi-well plate as claimed in claim 5 wherein the polymer has a weight/volume (w/v) percentage concentration of between about 0.1% to about 2.5%.

24. The multi-well plate as claimed in claim 5 wherein the polymer has a weight/volume (w/v) percentage concentration of between about 0.1% to about 2%.

25. The multi-well plate as claimed in claim 5 wherein the polymer has a weight/volume (w/v) percentage concentration of about 1%.

26. The multi-well plate as claimed in claim 1 wherein the substance is solid or semi-solid in use.

* * * * *